*(12)* United States Patent
Sander et al.

*(10)* Patent No.: US 6,350,911 B1
*(45)* Date of Patent: Feb. 26, 2002

(54) METHOD FOR PRODUCING AMINES

(75) Inventors: Michael Sander, Ruhland; Ulrich Penzel, Tettau, both of (DE); Hans Volkmar Schwarz, Waterloo (BE); Eckhard Ströfer, Mannheim (DE); Dieter Stützer, Dudenhofen (DE); Jörn Müller, Ludwigshafen (DE); Markus Maurer, Ludwigshafen (DE); Peter Zehner, Ludwigshafen (DE); Ekkehard Schwab, Neustadt (DE); Ralf Böhling, Griesheim (DE); Dominic Vanoppen, Fussgönheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/857,903

(22) PCT Filed: Dec. 9, 1999

(86) PCT No.: PCT/EP99/09680

§ 371 Date: Jun. 11, 2001

§ 102(e) Date: Jun. 11, 2001

(87) PCT Pub. No.: WO00/35852

PCT Pub. Date: Jun. 22, 2000

(30) Foreign Application Priority Data

Dec. 12, 1998 (DE) ......................... 198 57 409
Jul. 14, 1999 (DE) ......................... 199 32 821

(51) Int. Cl.⁷ ..................... C07C 211/00; C07C 209/00
(52) U.S. Cl. ................. 564/305; 564/308; 564/415; 564/418; 564/422; 564/423
(58) Field of Search .................. 564/305, 308, 564/415, 418, 422, 423

(56) References Cited

U.S. PATENT DOCUMENTS

| 2,823,235 A | 2/1958 | Graham et al. |
| 3,636,152 A | 1/1972 | Szigeth |
| 4,192,856 A | 3/1980 | Rapp et al. |
| 4,212,824 A | 7/1980 | Seagraves |
| 4,482,696 A | 11/1984 | Schuster et al. |
| 4,740,621 A | 4/1988 | Adams et al. |
| 5,387,396 A | 2/1995 | Dallmeyer et al. |
| 5,563,296 A | 10/1996 | Zarnack et al. |

FOREIGN PATENT DOCUMENTS

| CA | 1211757 | 9/1986 |
| DE | 1809711 | 7/1969 |
| DE | 2135154 | 2/1973 |
| DE | 2736872 | 2/1979 |
| DE | 3636984 | 5/1987 |
| EP | 0124010 | 11/1984 |
| EP | 263935 | 4/1988 |
| EP | 634391 | 1/1995 |
| GB | 1452466 | 10/1976 |

OTHER PUBLICATIONS

PCT International Search Report Dated Mar. 15, 2000.

*Primary Examiner*—Alan Siegel
(74) *Attorney, Agent, or Firm*—Fernando A. Borrego; Mary K. Cameron

(57) ABSTRACT

The invention relates to a process for the preparation of amines by hydrogenation of nitro compounds, which comprises carrying out the hydrogenation in a vertical reactor whose length is greater than its diameter, having a downward-facing jet nozzle arranged in the upper region of the reactor through which the starting materials and the reaction mixture are fed in, and having an outlet at any desired point of the reactor, through which the reaction mixture is fed back to the jet nozzle in an external circuit by means of a conveying means, and having flow reversal in the lower region of the reactor.

14 Claims, 1 Drawing Sheet

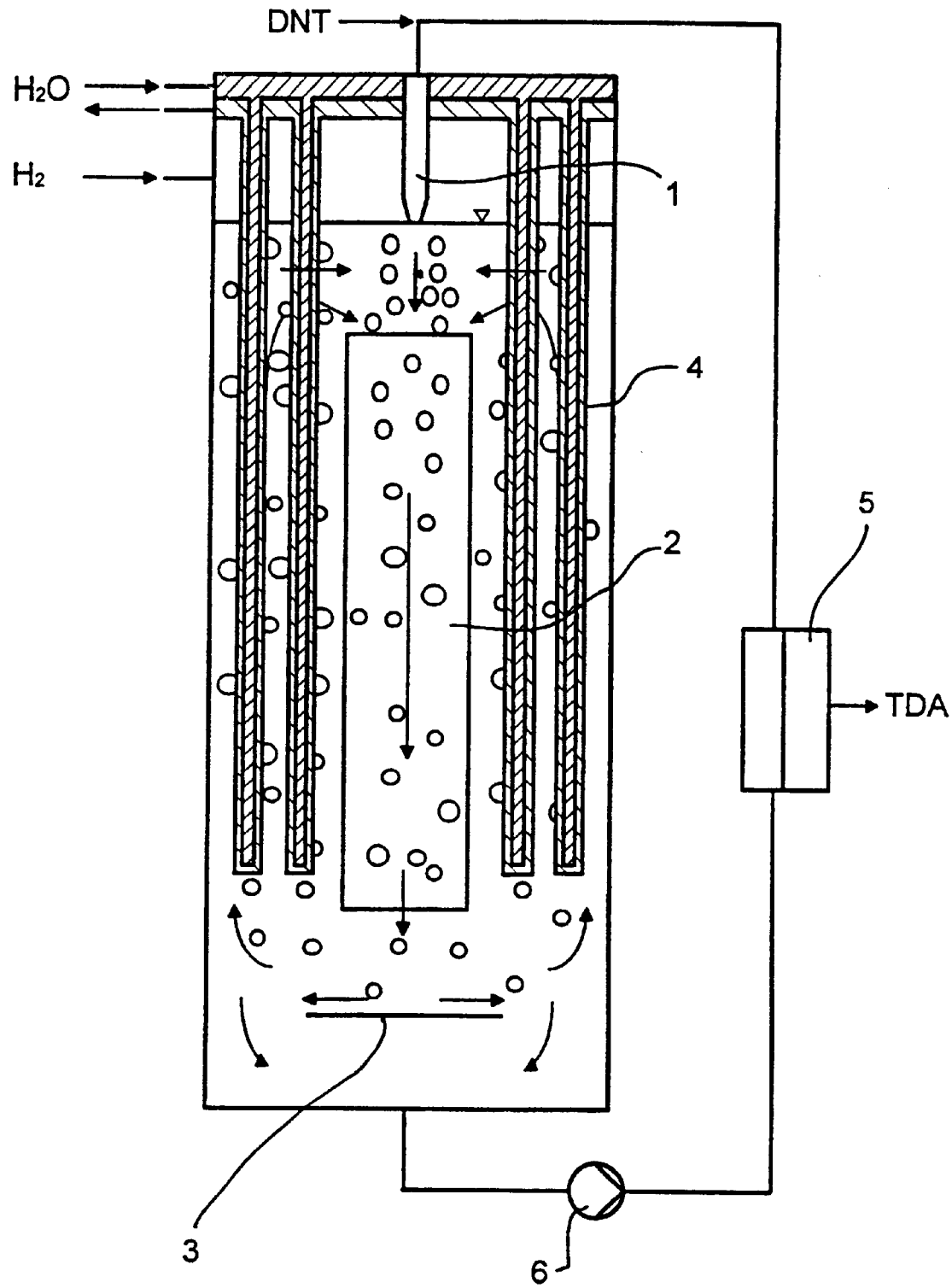

METHOD FOR PRODUCING AMINES

This application is a 371 of PCT/EP99/09680 filed Dec. 9, 1999.

The present invention relates to a continuous process for the preparation of amines, in particular aromatic amines, by catalytic hydrogenation of the nitro compounds on which the amines are based.

The preparation of amines, in particular aromatic mono and/or polyamines, by catalytic hydrogenation of the corresponding mono and/or polynitro compounds has been known for some time and has been described many times in the literature.

In the preparation of aromatic mono and/or polyamines which is conventional in the art by reaction of nitro compounds with hydrogen, a considerable amount of heat is liberated. In industry, the hydrogenation is therefore usually carried out at very low temperatures in the liquid phase in the presence of hydrogenation catalysts. The compound to be reduced is mixed with the catalyst in a solvent and reduced batchwise in an autoclave or continuously in a loop reactor, a bubble column or a reactor cascade. These known processes have a number of disadvantages, for example the necessity to remove the deactivated catalyst fractions, in particular in continuous processes, which results in catalyst losses. Furthermore, the side reactions which frequently occur, result in the formation of interfering substances, for example tar-like constituents, and thus in reductions in yield, are a problem in many processes used hitherto.

In order to reduce these disadvantages, it is known to arrange the catalyst in a fixed bed. For example, DE-A 2 135 154 describes the hydrogenation of a nitro compound, alone or in the presence of a diluent, in the liquid state in a tubular reactor in the presence of a palladium catalyst on spinel in a fixed bed. Preparation of this palladium catalyst on spinel is very complex, and targeted immobilization on the support is only possible in some cases. Furthermore, this fixed-bed hydrogenation results in low hydrogenation yields and in the formation of high-boiling byproducts. Mention may be made by way of example in this connection of hydrogenolytic cleavage, ring hydrogenations or the formation of high-molecular-weight, tar-like substances. As a consequence of the highly exothermic force of the nitro group reaction and the high reaction rate at elevated temperatures, explosive side reactions can also occur.

In order to exclude these undesired side reactions as far as possible, industrial-scale hydrogenation of aromatic nitro compounds is therefore carried out at relatively low temperatures.

EP-A-124 010 describes a process for the preparation of aromatic diamines by catalytic hydrogenation of the corresponding dinitro compounds with simultaneous generation of steam at a pressure of >1 bar above atmospheric. The reactor used is a bubble column fitted with Field tubes. A reaction suspension essentially consisting of an aromatic dinitro compound, the corresponding diamine, a hydrogenation catalyst, a saturated, aliphatic alcohol having 1 to 6 carbon atoms as solvent and water is fed into the reactor with hydrogen. The amount of reaction suspension fed into the bubble column and the pressure, the temperature, and the amount of cooling water are set so that reaction temperature in the bubble column is from 140 to 250° C. The catalysts used are known hydrogenation catalysts, preferably metals from sub-group VIII of the Periodic Table, in particular Raney iron, cobalt and nickel.

The process described in EP-A-124 010 has the disadvantage that large amounts of solvent are used; although they do not produce the problems in the hydrogenation of polynitro compounds at elevated temperatures, they are not totally inert under the hydrogenation conditions, which results in undesired byproducts and reductions in yield.

EP-A-263 935 describes stirred-tank reactors for carrying out exothermic reactions which are distinguished by the fact that the reactors are cooled by means of water which is converted into steam in Field tubes. Field-tube heat exchangers are characterized by a high ratio between the heat-exchanger surface area and the volume of the reaction space and are thus particularly effective in dissipating heat of reaction that has been liberated. However, the process described in EP-A-263 935 is only of limited applicability for catalytic hydrogenations since there is no guarantee of optimum phase mixing. In particular, a high hydrogen concentration above the reaction mixture must always be ensured in order to guarantee continued dissolution of hydrogen in the reaction mixture. Nevertheless, zones with partial depletion of hydrogen form in the reactor. Owing to the inhomogeneities to be expected, uncontrollable side reactions take place to an increased extent, with losses of yield. In addition, the cooling surfaces become coated with high-molecular-weight compounds and/or catalyst components. In addition, the catalyst is subjected to high mechanical stresses in this process, which results in a reduced service life of the catalyst.

EP-A-634 391 describes a process for the hydrogenation of aromatic polynitro compounds to amines in which the abovementioned problems of hydrogenation of aromatic polynitro compounds are said to be minimized through technological optimization using a loop Venturi reactor with an ejector coupled with specific conditions, such as a precise circulation volume ratio, precise energy input and a precisely adjusted hydrogen volume flow rate. The catalysts used are the compounds described in EP-A-124 010.

In this process, the fact that a heat exchanger for dissipating the heat of reaction is arranged outside the loop reactor, local overheating can occur in the ejector and in the reactor, with immediate initiation of side reactions, such as ring hydrogenations, hydrogenolytic cleavage of the formation of high-molecular-weight, tar-like products which coat the catalyst surface. In addition, a pure bubble-column characteristic with respect to the flow and residence-time behavior, in which random small- and large-volume vortexes with comparatively low material transfer performance occur, becomes established in the reactor volume outside the ejector. There is therefore virtually no significant improvement in hydrogenation yield, hydrogenation selectivity and space-time yield in this process. In addition, the pumping of the entire reaction mixture again means that the catalyst here is subjected to high mechanical stresses, which again results in a reduced service life of the catalyst.

GB-A-1 452 466 describes a process for the hydrogenation of nitrobenzene in which an adiabatic reactor is installed downstream of an isothermal reactor. The majority of the nitrobenzene is reacted in a thermostatted tube-bundle reactor, with only the residual nitrobenzene being hydrogenated in an adiabatic reactor at a relatively low hydrogen excess of less than 30:1. However, this process is technically very complex.

DE-B-1 809 711 relates to the homogeneous introduction of liquid nitro compounds into a hot gas stream by atomization, preferably at narrowed points immediately before the reactor. However, the process reveals that, in spite of a considerable hydrogen excess, a large part of the reaction enthalpy does not leave the reactor with the product gas, resulting in cooling problems.

DE-A-36 36 984 describes a process for the coupled production of nitroaromatic and dinitroaromatic compounds from the corresponding aromatic hydrocarbons by nitration followed by hydrogenation. The hydrogenation is carried out in the gas phase at from 176 to 343.5° C. The hydrogen stream in this process also serves to dissipate the heat of reaction from the reactors. The gas-phase hydrogenation apparatus described essentially consists of two reactors connected in series with cooling and starting-material feed in between; however, their size is not discussed. The temperature profile of the reactors reveals, however, that a not inconsiderable part of the heat of reaction does not leave the reactor with the product gas stream owing to the low heat capacity of the hydrogen. A further disadvantage of this process is the energy-intensive evaporation of nitroaromatics.

It is an object of the present invention to develop a continuous process for the preparation of amines, in particular aromatic amines, by hydrogenation of nitro compounds, in particular aromatic nitro compounds, in the presence of hydrogenation catalysts, preferably supported metal catalysts, which uses a simple apparatus and in which the space-time yield and the hydrogenation selectivity are improved and local overheating, and consequently side reactions occurring to an increased extent, is avoided.

We have found that, surprisingly, this object is achieved by a process for the preparation of amines, in particular aromatic amines, by hydrogenation of the corresponding nitro compounds in a vertical, preferably cylindrical reactor whose length is greater than its diameter, having a downward-pointing jet nozzle arranged in the upper region of the reactor through which the starting materials and the reaction mixture are fed in, and having an outlet at any desired point of the reactor, preferably in the lower region, through which the reaction mixture is fed back to the jet nozzle in an external circuit by means of a conveying means, preferably a pump, and having flow reversal in the lower region of the reactor.

Accordingly, the present invention provides a process for the preparation of amines, in particular aromatic amines by hydrogenation of corresponding nitro aromatic compounds, which comprises carrying out the reaction in a vertical, preferably cylindrical reactor whose length is greater than its diameter, having a downward-facing jet nozzle arranged in the upper region of the reactor through which the starting materials and the reaction mixture are fed in, and having an outlet at any desired point of the reactor, preferably in the lower region, through which the reaction mixture is fed back to the jet nozzle in an external circuit by means of a conveying means, preferably a pump, and having flow reversal in the lower region of the reactor. The reactor described is referred to below as a loop reactor.

The flow reversal and thus the formation of internal loop flow can be effected, in the case of take-off of the reaction mixture in the upper region of the reactor, by impact of the injected reaction mixture on the reactor base. In the case of the preferred take-off of the reaction mixture in the lower region of the reactor, the flow reversal is achieved by internals, in particular a baffle plate perpendicular to the reactor wall.

In a preferred embodiment of the novel process, the loop reactor has a preferably concentric spigot parallel to the reactor wall between the nozzle and the flow reversal. This spigot can be in the form of a simple tube, a tubular plate heat exchanger or a coiled cooling tube.

The concentric spigot in combination with the baffle plate stabilizes the loop flow within the reactor, referred to below as internal loop flow. Besides producing flow reversal, the baffle plate makes sure that no gas bubbles are dragged into the external loop flow and damage the pump.

The fact that the diameter of the loop reactor is smaller than its height produces adequate loop flow throughout the reactor and prevents the formation of dead zones.

In a further preferred embodiment of the invention, the reactor has integrated heat exchangers in the reactor interior. These heat exchangers should be of such a design that they do not prevent internal loop flow and do not cause turbulence. Examples of heat exchangers which can be used are tubes carrying cooling medium, which are preferably parallel to the reactor wall, plate heat exchangers, which are preferably parallel to the reactor wall, or boiling tubes closed at the bottom, as described in EP-A-263 935, known as Field tubes. If Field tubes are used, it is possible to utilize the steam formed as process steam.

In this embodiment, the reactor used in accordance with the invention can be regarded as a reaction heat exchanger since the heat of reaction is dissipated at the point where it is formed. It is also possible to install a heat exchanger in the external loop flow in addition to the heat exchangers integrated in the reactor.

The majority of the reaction mixture is transported in the internal loop flow; only a small proportion of the reaction mixture is pumped externally, thus providing the drive for the loop flow. The ratio between the volume flow rates of the internal loop flow and the external loop flow is from 2:1 to 30:1, preferably from 5:1 to 10:1.

The low proportion of external loop flow in the reaction mixture as a whole means that significantly lower amounts of catalyst are circulated per time unit via the circulation pump than in the case of cooling via an external heat exchanger. This results in a reduction in the mechanical stress on the catalyst and thus in a longer service life of the catalyst. In addition, this embodiment, in combination with integrated heat exchangers, ensures high isothermicity of the reaction, i.e. a very small temperature gradient over the reactor height, since the hydrogenation proceeds virtually completely in the internal loop flow and the heat of reaction is therefore dissipated right where it is generated. It virtually eliminates restrictions on the reaction rate due to material and heat transport. Side reactions favored by temperature gradients in the reaction system are suppressed virtually totally. The reaction rate is then only limited by the reaction kinetics. In addition, the safety of the process is improved compared with cooling in an external circuit, since the reactor cooling continues to function even if the pump for the external circuit fails.

The jet nozzle can be designed as a one- or two-component nozzle. In the case of the one-component nozzle, only the liquid reaction mixture is injected through the nozzle, and the hydrogen is fed into the reactor at any other desired point, but preferably in the liquid phase. This embodiment has the advantage of simple construction of this nozzle, but the disadvantage of poor dispersal of the hydrogen in the reaction mixture. In the case of the two-component nozzle, which is of more complex design, the hydrogen is fed in and dispersed in the center of the nozzle. In this embodiment of the process, the dispersal of the hydrogen in the reaction mixture is significantly better. It can be virtually excluded that partial depletion in hydrogen occurs in individual zones of the reactor.

It is preferred, irrespective of the type of nitro compounds employed, to maintain a pressure of from 5 to 100 bar, preferably from 10 to 50 bar, and an operating temperature of from 80 to 200° C., preferably from 100 to 150° C., in the reactor. The power input is preferably from 15 to 30 kW/l at the nozzle, and from 3 to 10 W/l in the reaction system as a whole.

The product is discharged from the system continuously at any desired point, but preferably in the lower region of the reactor at its base or in particular from the external loop flow via a catalyst separation unit or without one. This separation unit can be a gravity separator, for example a settler, a suitable filter, for example a cross-flow filter, or a centrifuge. The catalyst can be separated from the product and then fed back into the reactor system. The product is preferably discharged with retention of the catalyst. The amine can then be purified by conventional and known methods, for example by distillation or extraction.

A post-reactor for completion of the reaction can be located between the reaction mixture outlet and the separation unit. This post-reactor can have the same design as a novel reactor, and at least one stirred reactor and/or flow tube can also be used.

In the novel process, the mono- and/or polynitro compound is employed in pure form, as a mixture with the corresponding mono- and/or polyamine, as a mixture with the corresponding mono- and/or polyamine and water or as a mixture with the corresponding mono- and/or polyamine, water and a solvent, in particular an alcoholic solvent. The aromatic mono and/or polynitro compound is introduced into the mixture in finely divided form. The nitro compound is preferably introduced into the jet nozzle, particularly preferably into the mixing chamber of the nozzle.

Use is preferably made in the novel process of aromatic nitro compounds having one or more nitro groups and 6 to 18 carbon atoms, for example nitrobenzenes, for example nitrobenzene, 1,3-dinitrobenzene, nitrotoluenes, for example 2,4 or 2,6-dinitrotoluene, 2,4,6-trinitrotoluene, nitroxylenes, for example 1,2-dimethyl-3-, 1,2-dimethyl-4-, 1,4-dimethyl-2-, 1,3-dimethyl-2-, 2,4-dimethyl-1- and 1,3-dimethyl-5-nitrobenzene, nitronaphthalenes, for example 1-, 2-nitronaphthalene, 1,5 and 1,8-dinitronaphthalene, chloronitrobenzenes, for example 2-chloro-1,3- and 1-chloro-2,4-dinitrobenzene, o-, m- and p-chloronitrobenzene, 1,2-dichloro-4-, 1,4-dichloro-2-, 2,4-dichloro-1- and 1,2-dichloro-3-nitrobenzene, chloronitrotoluenes, for example 4-chloro-2, 4-chloro-3-, 2-chloro-4- and 2-chloro-6-nitrotoluene, nitroanilines, for example o-, m- and p-nitroaniline; nitroalcohols, for example tris(hydroxymethyl)-nitromethane, 2-nitro-2-methyl- and 2-nitro-2-ethyl-1,3-propanediol, 2-nitro-1-butanol and 2-nitro-2-methyl-1-propanol, and any desired mixtures of two or more of said nitro compounds.

The novel process is preferably used to hydrogenate aromatic nitro compounds, preferably mononitrobenzene, methylnitrobenzene or methylnitrotoluene, and in particular 2,4-dinitrotoluene or technical-grade mixtures thereof with 2,6-dinitrotoluene, where these mixtures preferably contain up to 35% by weight, based on the total mixture, of 2,6-dinitrotoluene with proportions of from 1 to 4 percent of vicinal DNT and from 0.5 to 1.5% of 2,5- and 3,5-dinitrotoluene, to the corresponding amines.

The novel process is particularly advantageous in the hydrogenation of dinitrotoluene isomers to the corresponding tolylenediamine (TDA) derivatives and in the hydrogenation of mononitrobenzene to aniline. The formation of high-molecular-weight, tar-like byproducts, which resulted in reductions in yield and in the formation of agglomerates and thus in premature deactivation of the catalyst in the prior-art processes, can be suppressed virtually completely. Purification of the aromatic amines formed, in particular of the TDA, is thus also less complicated than in the prior-art processes.

The hydrogenation of the dinitrotoluene and the mononitrobenzene can be carried out in solution. The solvents used are the usual substances for this purpose, in particular lower alcohols, preferably ethanol. Owing to the optimum flow conditions and the immediate dissipation of the heat of reaction in the reactor used in accordance with the invention, it is also possible to carry out the hydrogenation without a solvent. This has the advantages that the volume of the reaction mixture is smaller, which enables the reactor, pumps and pipelines to be smaller, that side reactions between the solvent and the starting materials are excluded, and that the effort in working up the final products is reduced.

The novel process is carried out using hydrogenation catalysts known per se for aromatic nitro compounds. It is possible to use homogeneous and/or in particular heterogeneous catalysts. The heterogeneous catalysts are employed in the finely divided state and are suspended in the reaction suspension in the finely divided form. Suitable catalysts are metals from sub-group VIII of the Periodic Table, which may be supported on support materials such as activated carbon or oxides of aluminum, silicon or other materials. Preference is given to Raney nickel and/or supported catalysts based on nickel, palladium and/or platinum.

In a particularly advantageous embodiment of the process according to the invention for the preparation of aromatic amines, the catalyst used is a platinum/iron catalyst supported on carbon. The carbon support employed is, in particular, a hydrophobic carbon. Activated carbon or acetylene black is preferably used. The platinum is usually on the support in the form of the metal. The iron is usually in the form of an iron compound, preferably as iron(III) oxide. The platinum is usually present in an amount in the range from 0.1 to 10% by weight, based on the weight of the support, and the iron is usually present in an amount in the range from 0.1 to 10% by weight, calculated as iron(III) oxide and likewise based on the support.

The catalyst is prepared by conventional and known processes, as described, for example, in U.S. Pat. No. 2,823,235.

Surprisingly, it has been found that on use of the preferred catalyst for carrying out the process according to the invention, particularly high space-time yields and particularly high selectivity of the hydrogenation, in particular substantial suppression of ring hydrogenation, can be achieved. Thus, the catalyst preferably used enables a space-time yield of 2 300 kg of aniline/$(m^3*h)$ and a selectivity of 99.9 to be achieved in the hydrogenation of mononitrobenzene in a reactor according to the invention at a reaction temperature of 180° C., while under the same conditions using a zeolite-supported nickel catalyst, a space-time yield of only 1 500 kg of aniline/$(m^3*h)$ and a selectivity of less than 98% were achieved. Furthermore, the deactivation of the catalyst preferably employed is significantly less compared with other catalysts. Thus, it was possible to prepare 10 kg of aniline using 1 g of a catalyst preferred in accordance with the invention, while it was only possible to prepare 0.8 kg of aniline in the case of a zeolite-supported nickel catalyst.

The dispersal of the individual reactants achieves, in combination with the other reaction parameters, intensive mixing of all components at low substrate concentrations, high material-transfer coefficients and large volume-specific phase interfaces. The arrangement of the cooling tubes in the reactor parallel to the reactor walls results in their being virtually no reaction-temperature gradients of the reactor contents.

Prevention of local overheating means that side reactions are significantly suppressed and catalyst deactivation substantially avoided. High space-time yields at high selectivities are thus achieved, even at low catalyst concentrations. Owing to the presence of an external pumped circuit and the mixing ratios in the reactor, the loop reactor has the characteristics of a stirred reactor with respect to its residence-time behavior.

As described above, the novel process is particularly suitable for the hydrogenation of dinitrotoluene to tylenediamine. In this reaction in particular, the prior-art processes result in pronounced side reactions with the formation of tar-like constituents. The preparation of tolylenediamine by the novel process is carried out at the usual temperatures and pressures mentioned above for the preparation of aromatic amines. The ratio between dinitrotoluene feed and the external loop flow is preferably in the range from 1 t of dinitrotoluene per 50 $m^3$ of reaction mixture in the external circuit to 1 t of dinitrotoluene per 60 $m^3$ of reaction mixture in the external circuit. This amount of dinitrotoluene is added to the reaction mixture at any desired point, preferably into the external loop flow, particularly preferably in or just before the nozzle.

The tolylenediamine can likewise be discharged at any desired point, in particular from the external loop flow before the dinitrotoluene feed point. Since the hydrogenation of the dinitrotoluene takes place virtually quantitatively under said condition in the internal loop stream, the external loop stream essentially consists, before the dinitrotoluene feed point, of pure tolylenediamine, water, possible solvent and catalyst. The tolylenediamine is separated from the discharged stream and fed to purification, while the catalyst and any water are fed back to the external loop stream.

Owing to the low concentration of dinitrotoluene in the reaction mixture, explosive mixtures cannot form.

The hydrogenation of the dinitrotoluene is preferably carried out at from 80 to 200° C. and at from 10 to 50 bar.

The tolylenediamine prepared by the novel process is very pure. The formation of tar-like constituents can be suppressed virtually completely. Their proportion is usually significantly below 1% by weight, based on the tolylenediamine. Space-time yield in the novel process is greater than 500 g/l/h.

The invention is illustrated in greater detail with reference to the example below.

EXAMPLE 1

A cylindrical reactor having an external circuit, a baffle plate in the lower part of the reactor and a concentric spigot, as shown in the drawing, is used. The reaction volume of the reactor is around 0.05 $m^3$. The reactor is provided with 36 Field tubes connected in parallel, corresponding to a total cooling surface area of about 2.5 $m^2$. The amount of cooling water fed into the Field tubes was 1 $m^3$/h, the temperature of the cooling water fed into the Field tubes was 30° C. and the discharge temperature of the cooling water was 90° C.

By means of a high-pressure pump, 40.3 kg/h of a dinitrotoluene melt consisting of 80 parts by weight of 2,4-dinitrotoluene and 20 parts of 2,6-dinitrotoluene were injected at 120° C. through the nozzle into a fast-flowing mixture of about 62 parts by weight of a corresponding diaminotoluene mixture, 36 parts by weight of water and 2 parts by weight of a finely divided Ni hydrogenation catalyst. A pressure of 25 bar was maintained in the reactor by simultaneous introduction of 30 $m^3$ (s.t.p.)h of hydrogen. In order to maintain the loop stream, a volume flow rate of 2.6 $m^3$/h was circulated in the external product circuit. A pressure of around 3 bar prevailed in the reaction nozzle, and the power input was 5 kW/$m^3$. The reaction proceeded under virtually isothermal conditions, since the heat of reaction was dissipated right where it was formed. The maximum reaction temperature in the lower third of the reactor was 122° C. Simultaneously, with retention of the catalyst, 26.7 kg/h of a corresponding diaminotoluene mixture and 15.8 kg/h of water were removed continuously from the reactor, corresponding to a space-time yield of 580 kg of amine mixture/$m^3$*h. The yield of diamine was >99%, based on the dinitrotoluene employed. Distillative work-up produced 0.15% of low-boiling byproducts ("low boilers") and 0.75% of tar-like products ("high boilers"). The content of nitro and aminonitro compounds in the product stream was below the detection limit of 10 ppm. There was no evidence of any significant deactivation of the hydrogenation catalyst employed for the operating state described above, even after a reaction time of 100 hours.

EXAMPLE 2

A cylindrical reactor having an external circuit, a baffle plate in the lower part of the reactor and a concentric spigot, as shown in the drawing, is used. The reaction volume of the reactor is around 0.05 $m^3$. The reactor is provided with 36 Field tubes connected in parallel, corresponding to a total cooling surface area of about 2.5 $m^2$. The amount of cooling water fed into the Field tubes was 2.5 $m^3$/h, the temperature of the cooling water fed into the Field tubes was 30° C. and the discharge temperature of the cooling water was about 90° C.

By means of a high-pressure pump, 134 kg/h of liquid mononitrobenzene were injected at 180° C. into a fast-flowing mixture of about 71 parts by weight of aniline, 27 parts by weight of water and 2 parts by weight of a finely divided Pt/Fe/C hydrogenation catalyst. A pressure of 30 bar was maintained in the reactor by simultaneous introduction of 75 $m^3$ (s.t.p.)/h of hydrogen. In order to maintain the loop stream, a volume flow rate of 2.6 $m^3$/h was circulated in the external product circuit. A pressure of around 3 bar prevailed in the reaction nozzle, and the power input was 5 kW/$m^3$. The reaction proceeded under virtually isothermal conditions, since the heat of reaction was dissipated right where it was formed. The maximum reaction temperature in the lower third of the reactor was 182° C. Simultaneously, with retention of the catalyst, 101.3 kg/h of aniline and 39.2 kg/h of water were removed continuously from the reactor, corresponding to a space-time yield of 2 030 kg of aniline/$m^3$*h. The yield of aniline was, based on the mononitrobenzene employed, >99.5%. Distillative work-up produced cyclohexylamines and N-cyclohexylamines as byproducts in a concentration range from a few hundred to a thousand ppm. The concentrations of the cyclohexanols and cyclohexanones also produced as byproducts were comparatively lower. The content of mononitrobenzene in the product stream was below the detection limit of 10 ppm. There was no evidence of deactivation of the hydrogenation contact employed for the operating state described above after a reaction time of 30 hours.

We claim:

1. A process for the preparation of amines by hydrogenation of nitro compounds, which comprises carrying out the hydrogenation in a vertical reactor whose length is greater than its diameter, having a downward-facing jet nozzle (1) arranged in an upper region of the reactor through which starting materials and reaction mixture are fed in, and having an outlet at any desired point of the reactor, through which the reaction mixture is fed back to the jet nozzle in an external circuit by means of a conveying means (6), and having flow reversal in a lower region of the reactor, and heat exchangers (4) installed in the reactor.

2. A process as claimed in claim 1, wherein the outlet is located at a lower end of the reactor.

3. A process as claimed in claim 1, wherein the reactor comprises a baffle plate (3) arranged perpendicular to the reactor wall which is located in the lower region of the reactor.

4. A process as claimed in claim 1, wherein a concentric spigot (2) is installed in the reactor parallel to the reactor wall.

5. A process as claimed in claim 1, wherein the heat exchangers (4) employed are cooling tubes, plate heat exchangers and/or boiling tubes.

6. A process as claimed in claim 1, wherein the ratio between reaction mixture circulating in the reactor and pumped reaction mixture is from 2:1 to 30:1.

7. A process as claimed in claim 1, wherein the ratio between the reaction mixture circulating in the reactor and the pumped reaction mixture is from 5:1 to 10:1.

8. A process as claimed in claim 1, wherein the nitro compounds employed are aromatic nitro compounds.

9. A process as claimed in claim 8, wherein the nitro compounds employed are nitrobenzene and/or dinitrotoluene.

10. A process as claimed in claim 1, wherein the reaction is carried out in the presence of catalysts.

11. A process as claimed in claim 10, wherein the catalyst employed for the hydrogenation of the aromatic nitro compounds is a platinum/iron catalyst supported on carbon.

12. A process as claimed in claim 11, wherein the platinum is present in an amount from 0.1 to 10% by weight, based on the weight of the support, and the iron is present in an amount in the range from 0.1 to 10% by weight, calculated as iron (III) oxide, and based on the support.

13. A process as claimed in claim 1, wherein the hydrogenation of the aromatic nitro compounds is carried out in the range from 80 to 200° C.

14. A process as claimed in claim 1, wherein the hydrogenation of the aromatic nitro compounds is carried out at from 10 to 50 bar.

* * * * *